US009068996B2

(12) United States Patent
Pettigrew et al.

(10) Patent No.: US 9,068,996 B2
(45) Date of Patent: Jun. 30, 2015

(54) ANALYTE DETECTION METHOD

(75) Inventors: David Michael Pettigrew, Huntingdon (GB); Peter Georg Laitenberger, Cambridge (GB); Bo Liu, Cambridge (GB)

(73) Assignee: SPHERE MEDICAL LIMITED, Cambridge (GB)

( * ) Notice: Subject to any disclaimer, the term of this patent is extended or adjusted under 35 U.S.C. 154(b) by 116 days.

(21) Appl. No.: 13/878,815

(22) PCT Filed: Oct. 11, 2011

(86) PCT No.: PCT/GB2011/051952
§ 371 (c)(1),
(2), (4) Date: Jul. 24, 2013

(87) PCT Pub. No.: WO2012/049486
PCT Pub. Date: Apr. 19, 2012

(65) Prior Publication Data

US 2013/0302781 A1    Nov. 14, 2013

(30) Foreign Application Priority Data

Oct. 13, 2010   (GB) .................................. 1017256.7

(51) Int. Cl.
| | |
|---|---|
| *G01N 33/94* | (2006.01) |
| *G01N 33/50* | (2006.01) |
| *G01N 33/52* | (2006.01) |
| *G01N 33/557* | (2006.01) |

(52) U.S. Cl.
CPC ..... *G01N 33/948* (2013.01); *Y10T 436/203332* (2015.01); *Y10T 436/14* (2015.01); *G01N 33/52* (2013.01); *G01N 33/557* (2013.01)

(58) Field of Classification Search
CPC ..... G01N 33/948; G01N 33/94; G01N 33/50; G01N 33/00; Y10T 436/00; Y10T 436/11; Y10T 436/14; Y10T 436/21
USPC ...................................... 436/131, 127; 435/4
See application file for complete search history.

(56) References Cited

U.S. PATENT DOCUMENTS

| | | | |
|---|---|---|---|
| 5,906,742 | A | 5/1999 | Wang et al. |
| 6,831,733 | B2 | 12/2004 | Petterson et al. |
| 7,247,484 | B2 | 7/2007 | Wu et al. |
| 2012/0267259 | A1 | 10/2012 | Pettigrew et al. |

FOREIGN PATENT DOCUMENTS

| | | |
|---|---|---|
| WO | WO 2005/048126 A2 | 11/2004 |
| WO | WO 2010/017151 A1 | 2/2010 |

OTHER PUBLICATIONS

Svobodováet al.; The colour reaction of phenols with the Gibbs reagent; Microchimica Acta; 70(II/3-4); pp. 197-211; May 1978.
Ainashef et al.; Electrochemical Generation of Superoxide in Room-Temperature Ionic Liquids; Electrochemical and Solid-State Letters; 4(11):D16-D18; Nov. 2001.
Araki et al.; Antioxidative properties of probucol estimated by the reactivity with superoxide and by electrochemical oxidation; Chem Pharm Bull (Tokyo); 49(8):943-7; Aug. 2001.
Araki et al.; The mechanism of reaction of ebselen with superoxide in aprotic solvents as examined by cyclic voltammetry and ESR; Chem Pharm Bull (Tokyo); 49(5):541-5; May 2001.
Barr et al.; Propofol dosing regimens for ICU sedation based upon an integrated pharmacokinetic-pharmacodynamic model; Anesthesiology; 95(2); p. 324-333; Aug. 2001.
Beissenhirtz et al.; Comparing an in vitro electrochemical measurement of superoxide scavenging activity with an in vivo assessment of antioxidant potential in Chinese tonifying herbs; Phytother Res.; 18(2):149-53; Feb. 2004.
Beissenhirtz et al.; Immobilized Cytochrome c Sensor in Organic/Aqueous Media for the Characterization of Hydrophilic and Hydrophobic Antioxidants; Electroanalysis; vol. 15, Issue 18, pp. 1425-1435, Oct. 2003.
Campanella et al.; Superoxide dismutase biosensors working in non-aqueous solvent; Fresenius J Anal Chem.; 369(7-8):594-600; Apr. 2001.

(Continued)

*Primary Examiner* — Christine T Mui
(74) *Attorney, Agent, or Firm* — Shay Glenn LLP

(57) ABSTRACT

Disclosed is a method of determining the presence of an analyte of interest by means of a detection of a reaction product between the analyte of interest and a reactant, the method comprising extracting the analyte of interest from a complex sample matrix; transferring the analyte of interest to an initial reaction mixture; performing a background measurement on the initial reaction mixture comprising at most a negligible concentration of the reaction product, wherein the reaction conditions present in said initial reaction mixture at least reduce the reaction rate of the formation of the reaction product such that the background measurement can be performed without a measurable change in said negligible concentration; altering the reaction conditions in the initial reaction mixture to accelerate said reaction rate; continuing said reaction until the concentration of the reaction product has stabilized; performing a second measurement on the resultant reaction mixture to obtain a signal correlated to said concentration; and determining the presence of the analyte of interest from a difference between the background measurement and the second measurement. In a preferred embodiment, the analyte of interest is Propofol (2,6-di-isopropylphenol), and the reactant is the activated Gibbs reagent (2,6-dichloroquinoneimine).

20 Claims, 3 Drawing Sheets

(56) References Cited

OTHER PUBLICATIONS

Figure 1:
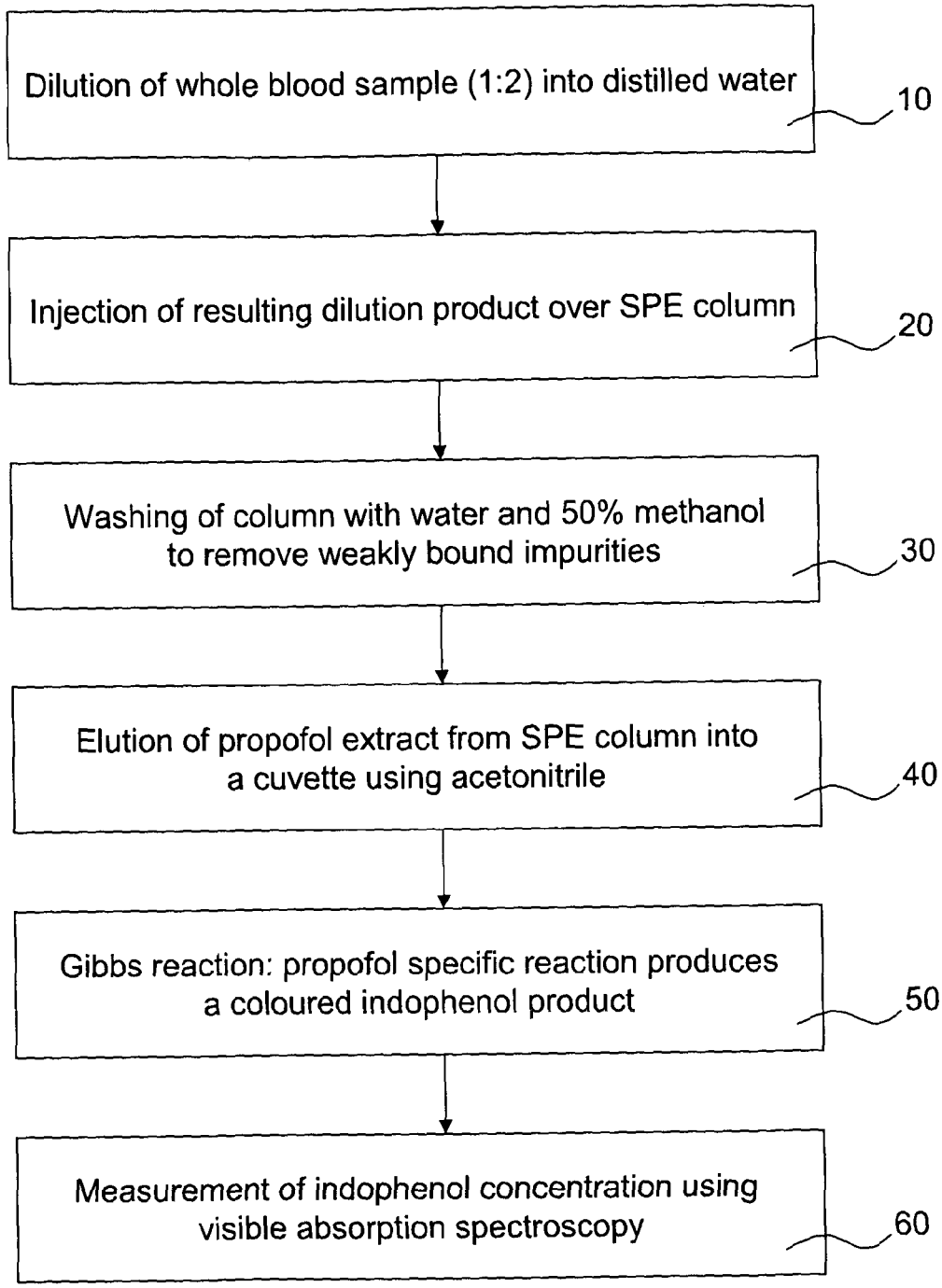

Cohen et al.; Quantitative measurement of propofol and in main glucuroconjugate metabolites in human plasma using solid phase extraction-liquid chromatography-tandem mass spectrometry; J Chromatogr B Analyt Technol Biomed Life Sci; 854(1-2); pp. 165-172; Jul. 2007.

Csallany et al.; ?-tocopherol oxidation mediated by superoxide anion I. Reactions in aprotic and protic conditions; Lipids; vol. 27, Issue 3, pp. 195-200; Mar. 1992.

Dawidowicz et al.; The advantages of cell lysis before blood sample preparation by extraction for HPLC propofol analysis; Biomed Chromatogr; 14(7); pp. 493-497; Nov. 2000.

Ezerskis et al.; Electropolymerization of chlorinated phenols on a Pt electrode in alkaline solution Part I: A cyclic voltammetry study; Journal of Applied Electrochemistry; vol. 31; Issue 10; pp. 1117-1124; Oct. 2001.

Ferreira et al.; Electrode passivation caused by polymerization of different phenolic compounds; Electrochimica Acta; vol. 52, Issue 2; pp. 434-442; Oct. 25, 2006.

Gibbs, H.D.; Phenol tests III. The indophenol test; Journal of Biological Chemistry, 72(2); pp. 649-664; 1927 (year of pub. sufficiently earlier than effective US filing date and any foreign priority date).

Gülçin et al.; Determination of in vitro antioxidant and radical scavenging activities of propofol; Chem Pharm Bull (Tokyo); 53(3):281-5; Mar. 2005.

Herath et al.; Electrochemical investigation of superoxide anion scavenging ability of 1,2,3-triketohydrindene hydrate in aprotic solvents; Electrochimica Acta; vol. 51; Issue 14; pp. 2890-2897; Mar. 15, 2006.

Heyne et al.; Investigation of singlet oxygen reactivity towards propofol; Photochem Photobiol Sci; 2(9):939-45; Sep. 2003.

Kohen et al.; Quantification of the overall reactive oxygen species scavenging capacity of biological fluids and tissues; Free Radic Biol Med.; 28(6):871-9; Mar. 15, 2000.

Korotkova et al.; Study of antioxidant properties by voltammetry; Journal of Electroanalytical Chemistry; vol. 518; Issue 1; pp. 55-60; Jan. 11, 2002.

McGaughran et al.; Rapid measurement of blood propofol levels: a proof of concept study; J Clin Monit Comput.; 20(2):109-15; Apr. 2006.

Miniati, Enrico; Assessment of phenolic compounds in biological samples; Ann lst Super Sanita; 43(4):362-8; (year of publication is sufficiently earlier than the effective U.S. filing date and any foreign priority date) 2007.

Murphy et al.; The antioxidant potential of propofol (2,6-diisopropylphenol); Br J Anaesth.; 68(6):613-8; Jun. 1992.

Pallagi et al.; Mechanism of the Gibbs reaction. Part 4.1 Indophenol formation via n-chlorobenzoquinone imine radical anions .; The Journal of Organic Chemistry; 64(18); pp. 6530-6540; Aug. 1999.

Plummer GF; Improved method for the determination of propofol in blood by high-performance liquid chromatography with fluorescence detection; J Chromatogr.; 421(1):171-6; Oct. 9, 1987.

Prieto-Simón et al.; Electrochemical biosensors as a tool for antioxidant capacity assessment; Sensors and Actuators B: Chemical; vol. 129, Issue 1, pp. 459-466; Jan. 29, 2008.

Renée et al.; Superoxide protonation by weak acids in imidazolium based ionic liquids; J Phys Chem B.; 113(9):2826-31; Mar. 5, 2009.

Shafer et al.; Pharmacokinetics and pharmacodynamics of propofol infusions during general anesthesia; Anesthesiology; 69(3); pp. 348-356; Sep. 1988.

Svobodováet al.; Colour reaction of phenols with the gibbs reagent. The reaction mechanism and decomposition and stabilisation of the reagent; Microchimica Acta; 67; pp. 251-264; May 1977.

Uebel et al.; Electrochemical determination of 2,6-diisopropylphenol after high-performance liquid chromatography of extracts from serum; J Chromatogr.; 526(1):293-5; Mar. 16, 1990.

Volti et al.; Antioxidant properties of propofol when oxidative stress sleeps with patients; EXCLI Journal; 5:25-32; Apr. 13, 2006.

Pettigrew et al.; U.S. Appl. No. 13/878,820 entitled "Analyte extraction apparatus and method," filed Apr. 11, 2013.

ANALYTE DETECTION METHOD

FIELD OF THE INVENTION

The present invention relates to a method for improving the detection of analytes in complex sample matrices, in situations where a reaction step is required to generate a product, which is subsequently detected. In particular, this invention provides a means for selectively measuring the concentration of the anaesthetic drug propofol in whole blood.

BACKGROUND OF THE INVENTION

Modern healthcare relies extensively on a range of chemical and biochemical analytical tests on a variety of body fluids to enable diagnosis, therapy and management of disease. Medical and technological advances have considerably expanded the scope of diagnostic testing over the past few decades. Moreover, an increasing understanding of the human body, together with the emergence of technologies, such as microsystems and nanotechnology, are expected to have a profound impact on diagnostic technology.

Increasingly, diagnostic tests in hospitals are carried out at the point-of-care (PoC), in particular, in situations where a rapid response is a prime consideration and therapeutic decisions have to be made quickly. Despite recent advances in PoC testing, several compelling needs remain unmet. For example, the detection of small molecules in biological samples is often very challenging, especially when no suitable receptor (e.g. enzyme, antibody, aptamer) with an appropriate specificity exists. The challenge is even greater when the molecule is lipophilic and a large proportion of the analyte is unavailable for analysis due to its association with hydrophobic components of the sample matrix, such as cells, lipids and proteins.

The detection of small molecules in complex media (e.g. blood, plasma, saliva, urine, waste water and their extracts) is often difficult due to the association of the analyte with components of the sample matrix (e.g. plasma proteins and lipid membranes). The free (unbound) molecule concentration (which can be in the picomolar range) is often below the sensitivity limits of the most commonly used measurement techniques (e.g. electrochemical, optical). For this reason, state of the art methods for small molecule detection in complex media often involve intensive sample preparation, such as dilution/extraction of the sample into an organic solvent, centrifugation, evaporation and analysis by high pressure liquid chromatography (HPLC). Depending on the specific characteristics of the analyte molecule, post-HPLC column detection of the eluted compound is performed using electrochemical or optical (absorption spectroscopy or fluorescence) methods, such as disclosed in G. F. Plummer, "Improved method for the determination of propofol in blood by high-performance liquid chromatography with fluorescence detection," *Journal of Chromatography*, vol. 421, 1987, p. 171 and in R. A. Uebel et al., "Electrochemical determination of 2,6-diisopropylphenol after high-performance liquid chromatography of extracts from serum," *Journal of Chromatography*, vol. 526, March 1990, pp. 293-5.

The complex and time-consuming nature of HPLC assays for small molecules in complex samples means that they are routinely performed by a very small number of specialist laboratories; for this reason the utility of these assays is rather limited. For example, for many drugs, such as propofol, there is a clear need to develop alternative, miniaturised assays. This would enable measurement and clinical intervention close to real time and at the point-of-care (PoC).

A method for detecting and measuring propofol in complex media has been described by McGaughran et al., "Rapid measurement of blood propofol levels: A proof of concept study," *Journal of Clinical Monitoring and Computing*, vol. 20, 2006, pp. 381-381. The disclosed method comprises solid phase extraction (SPE) of a diluted whole blood sample, followed by reaction with a phenol-specific (Gibbs) reagent, namely 2,6 dichloroquinone-4-chloroimide, to produce a strongly coloured indophenol product and detection of this same product by absorption spectroscopy.

The Gibbs/indophenol method has been successfully utilised for the detection of propofol. Here, specificity is achieved by the combination of the SPE step (specific for hydrophobic analytes), and the Gibbs reaction (specific for para-unsubstituted phenols, such as propofol, as for instance has been described by D. Svobodová at al., "Colour reaction of phenols with the Gibbs reagent. The reaction mechanism and decomposition and stabilisation of the reagent," *Microchimica Acta*, vol. 67, May. 1977, pp. 251-264, and by H. D. Gibbs, "Phenol tests III. The indophenol test," *Journal of Biological Chemistry* vol. 72, 1927, pp. 649-664.

Figure 2:
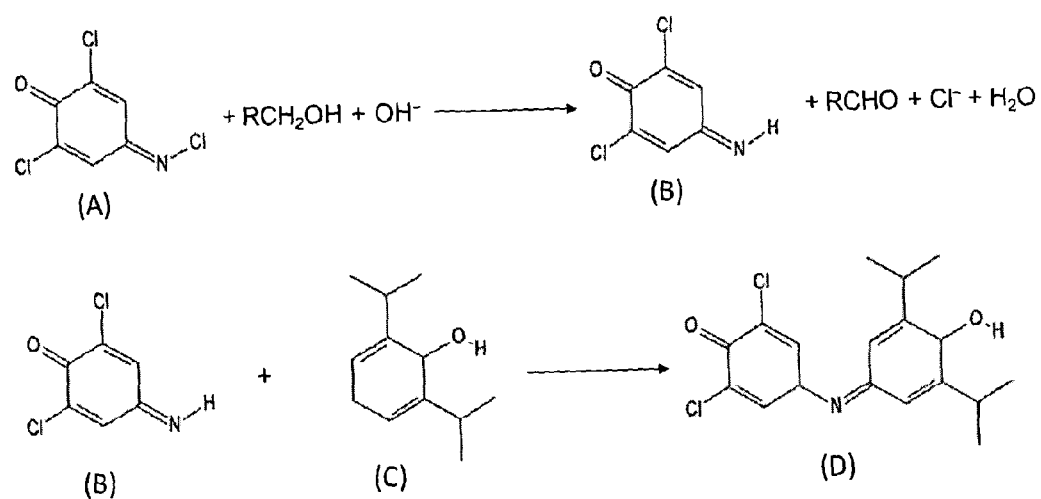

The overall process for the assay is described in FIG. 1, while the dominant reaction scheme for propofol conversion to the indophenol is shown in FIG. 2. As shown in FIG. 1, the process begins at step 10 in which a whole blood sample is diluted with distilled water in a ratio of 1:2. In step 20, the dilution product is injected over a SPE column, followed by a washing step 30 in which the SPE column is washed with a mixture of water and 50% methanol to remove weakly bound impurities. Next, propofol is extracted from the SPE column by elution with acetonitrile as shown in step 40, after which the Gibbs reaction is performed involving propofol as a reagent to produce a coloured indophenol product in step 50. To determine the propofol concentration in the original blood sample, the associated coloured indophenol concentration is determined in step 60 using visible absorption spectroscopy. It is noted that the Gibbs reaction is specific for all para-unsubstituted phenols including propofol. The potential for interference in the Gibbs reaction from other phenols is reduced by the SPE extraction step.

At sufficiently high pH and in the presence of a primary or secondary alcohol, the Gibbs reagent (A) is rapidly converted to an active form (B) which in turn reacts with propofol (C) to produce a coloured indophenol product (D), as shown in FIG. 2 and described in detail by D. Svobodová et al., "The colour reaction of phenols with the Gibbs reagent," *Microchimica Acta*, vol. 70, 1978, pp. 197-211. At a pH greater than 9.5, the rate of conversion of the Gibbs reagent (A) to the activated form (B) is much greater than the rate of reaction between propofol and the activated Gibbs reagent. In this case, the formation of the indophenol product from the reaction between the activated Gibbs reagent and propofol is the rate limiting step. Therefore, at high pH and when the concentration of the Gibbs reagent is in excess relative to propofol, the concentration of the indophenol product at equilibrium and the initial concentration of propofol in the sample are proportional to each other. Hence, an equilibrium measurement of the absorbance peak of the indophenol product at 595 nm, which by the Beer-Lambert law is directly proportional to the indophenol concentration, will give the initial propofol concentration in the sample before the reaction.

Testing of a device which utilises SPE and the Gibbs/indophenol reaction for propofol measurement has revealed excellent precision, linearity and accuracy for propofol concentrations down to 1 μg/ml in whole blood, as disclosed by McGaughran et al., "Rapid measurement of blood propofol levels: A proof of concept study," *Journal of Clinical Moni-*

*toring and Computing*, vol. 20, 2006, pp. 381-381. This limit of detection makes the device especially suitable for propofol measurements during surgical operations: during surgery, patients are usually administered sufficient propofol to ensure that the average blood propofol concentration is well above 2 µg/ml. For example, Schafer et al., "Pharmacokinetics and pharmacodynamics of propofol infusions during general anesthesia," *Anesthesiology*, vol. 69, September 1988, pp. 348-356, reported that patients required an average blood propofol concentration of 4.05+/−1.01 µg/ml for major surgery and 2.97+/−1.07 µg/ml for non-major surgery. Blood propofol concentrations at which 50% of patients (EC50) were awake and oriented after surgery were 1.07 and 0.95 µg/ml, respectively. This method and apparatus is more suited to use in these settings than the HPLC-based techniques, since the sample preparation is straight-forward, requiring only a simple blood sample dilution before introduction to the device. Furthermore, typical measurement times are much faster at approximately 3 to 5 minutes. Moreover, the instrument has a much smaller footprint and lower complexity than the equivalent HPLC device.

In settings where propofol is used for sedation, such as the intensive care unit (ICU), the propofol concentrations in whole blood are typically in the region of 0.25 to 2 µg/ml, as disclosed by J. Barr et al., "Propofol dosing regimens for ICU sedation based upon an integrated pharmacokinetic-pharmacodynamic model," *Anesthesiology*, vol. 95, 2001, p. 324. There is therefore a need to extend the lower limit of detection and measurement for the propofol assay described above. However, the optical measurement of propofol in whole blood below 1 µg/ml is limited by the presence of species in the blood sample that bind to and co-elute from the SPE column and absorb in the region of the indophenol signal.

In addition, insoluble aggregates can also be present and can scatter the light, thereby reducing the measured intensity at the detector. These species contribute to the measured absorbance spectrum in the region of the indophenol signal at 595 nm, causing an offset in the measured absorbance at this wavelength and limiting the ability of the instrument to measure accurately the propofol concentration in blood samples containing less than 1 µg/ml of propofol. As this non-propofol signal varies for different blood samples, this offset due to interfering species cannot be corrected for by applying, for example, correlation factors to the data. It is theoretically possible to correct for the extra absorbance signal using knowledge of a larger part of the absorbance spectrum (depending on the nature of the interfering species present). However, it would necessitate the use of expensive spectrometers to measure the absorbance signal either side of the absorbance peak of interest and interpolating the signal in order to subtract the background contribution to the peak. This, in turn, will increase the cost and complexity of the device.

SUMMARY OF THE INVENTION

The present invention seeks to provide a method of improving the lower limit of detection and/or concentration measurement of analytes, in particular propofol, in situations where a reaction step is required to generate a reaction product which is subsequently detected in order to qualitatively or quantitatively assess the presence of that analyte.

In accordance with a first aspect of the present invention, there is provided a method of determining the presence of an analyte of interest by means of a detection of a reaction product between the analyte of interest and a reactant, the method comprising performing a background measurement on the initial reaction mixture comprising at most a negligible concentration of the reaction product, wherein the reaction conditions present in said initial reaction mixture at least reduce the reaction rate of the formation of the reaction product such that the background measurement can be performed without a measurable change in said negligible concentration; altering the reaction conditions in the initial reaction mixture to accelerate said reaction rate; continuing said reaction until the concentration of the reaction product has stabilized; performing a second measurement on the resultant reaction mixture to obtain a signal correlated to said concentration; and determining the presence of the analyte of interest from a difference between the background measurement and the second measurement.

In accordance with the present invention, the rate of formation of the reaction product, e.g. the Gibbs-indophenol reaction product, is initially stopped or slowed down using appropriate measures, including, but not limited to, temperature, pH, slow mixing, the absence or removal of one or more reactant(s) and/or the addition of an inhibitor, in order to enable a reference measurement of the sample to be taken. The absence of the reaction or lower rate of reaction allows enough time to measure the level of the background "non-analyte" signal. Following the completion of the reference measurement, the reaction is allowed to proceed. Once the concentration of the target reaction product has stabilised, a second measurement, the sample measurement, is taken. In order to take account of the presence of the interfering species, the reference measurement is subsequently subtracted from the sample measurement in order to obtain an accurate estimation for the concentration of the target analyte.

In an embodiment, the method further comprises the steps of extracting the analyte of interest from a complex sample matrix; and transferring the analyte of interest to an initial reaction mixture.

In another embodiment, the step of determining the presence of the analyte of interest comprises determining the concentration of the analyte of interest in said reaction mixture.

The first and second measurements may be selected from one of optical, fluorescent, adsorption, colorimetric, electrochemical and gravimetric measurements.

Preferably, the step of performing the background measurement comprises measuring at least a part of the absorption spectrum of the initial reaction mixture; and the step of performing the second measurement comprises measuring at least a part of the absorption spectrum of the resultant reaction mixture.

In a particularly suitable embodiment, the analyte of interest is Propofol (2,6-di-isopropylphenol), and the reactant is the activated Gibbs reagent (2,6-dichloroquinoneimine). The initial reaction mixture may comprise the Gibbs reagent (2,6 dichloroquinone-4-chloroimide), wherein the reaction conditions in the initial reaction mixture comprise a pH that is sufficiently low to prevent the conversion of the Gibbs reagent into the activated Gibbs reagent, and wherein the step of altering the reaction conditions in the initial reaction mixture to accelerate said reaction rate comprises increasing the pH of the initial reaction mixture.

The initial reaction mixture may further comprise a buffer solution to maintain the sufficiently low pH, such as a citric acid buffer, a formic acid buffer or a bicarbonate buffer.

The first and second measurements may comprise determining the absorbance of the initial reaction mixture and the resultant reaction mixture respectively from an absorbance spectrum including the 400-800 nm interval.

The first and second measurements may comprise determining the absorbance of the initial reaction mixture and the resultant reaction mixture respectively at a first wavelength of 595 nm and a second wavelength of 800 nm.

More specifically, the first and second measurements may comprise determining the absorbance of the initial reaction mixture and the resultant reaction mixture respectively at a wavelength of 595 nm only.

The method may further comprise extracting the Propofol from the complex sample matrix using solid phase extraction. The complex sample matrix may be blood. The extraction step may comprise passing said blood sample over a solid phase extraction column, washing said column and eluting the Propofol using a suitable solvent. The solvent preferably is acetonitrile.

In an embodiment, the blood sample is diluted with water to a ratio of greater than 1:1 prior to passing it over said column, said ratio preferably lying in a range of 1:2-1:50 blood:water.

The method may further comprise performing at least one intermediate measurement following the step of altering the reaction conditions in the initial reaction mixture to accelerate said reaction rate and before the concentration of the reaction product has stabilized, wherein the step of determining the presence of the analyte of interest from a difference between the background measurement and the second measurement comprises measuring determining said presence from a difference between the background measurement, the second measurement and the at least one intermediate measurement.

BRIEF DESCRIPTION OF THE EMBODIMENTS

Figure 3:
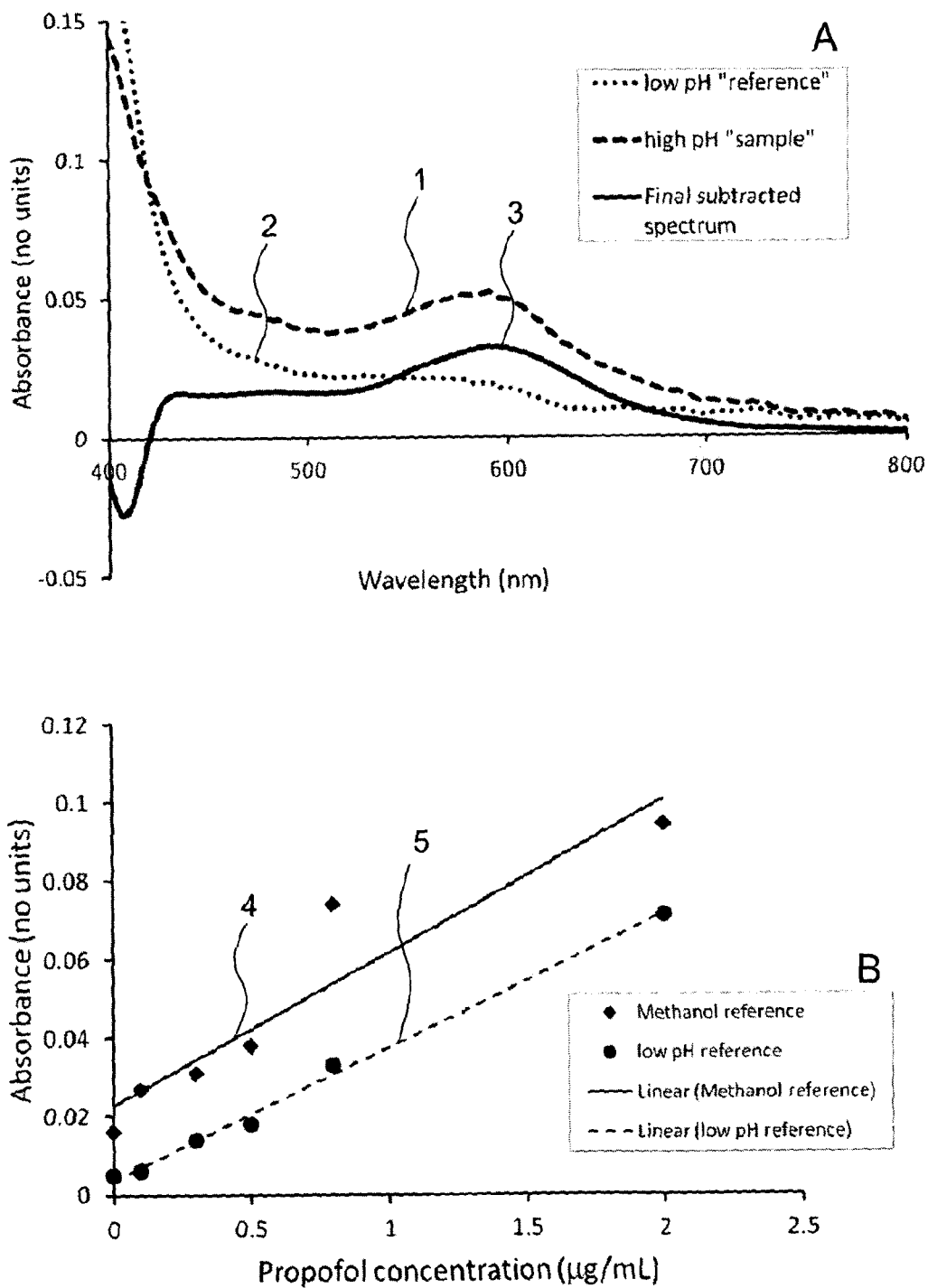

Embodiments of the invention are described in more detail and by way of non-limiting examples with reference to the accompanying drawings, wherein:

FIG. 1 schematically depicts the steps of operating a Gibbs/indophenol Propofol assay;

FIG. 2 schematically depicts the Gibbs/Indophenol reaction applied to propofol; and FIG. 3 schematically depicts background subtraction (A) and signal improvements (B) in a propofol assay employing an embodiment of the method of the present invention.

DETAILED DESCRIPTION OF THE DRAWINGS

It should be understood that the Figures are merely schematic and are not drawn to scale. It should also be understood that the same reference numerals are used throughout the Figures to indicate the same or similar parts.

Embodiments of the present invention can be applied to situations where a reaction step is required to generate a reaction product which is subsequently detected in order to qualitatively or quantitatively assess the presence of the target analyte. In general, the invention consists of the following steps (summarized below and in FIG. 1):

1. An extract of the complex medium is prepared, comprising the analyte of interest. Methods of extraction will be specific to the analyte of interest and will be known to those who are skilled in the art. The composition of this extract should be compatible with the desired reaction and subsequent detection of the reaction product of interest. Depending on the method of exchange (e.g. SPE), some purification of the analyte relative to any species that may interfere with the measurement is achieved at this stage.

In a preferred embodiment, a whole blood extract containing propofol is produced by passing a diluted whole blood sample (blood diluted with water in a ratio of greater than 1:1 blood:water, preferably 1:2 to 1:50 blood:water) over a SPE column (e.g. containing a suitable reverse phase material), washing the column, for example, with a 50% methanol solution and finally eluting using acetonitrile. In another embodiment, undiluted blood may be applied to the SPE column directly without dilution and the washing and elution steps performed in the same way.

2. Transfer of the extract of the complex medium, which contains the analyte of interest, to a reaction/analyte detection module. This module may be either separate from or connected directly to the extraction apparatus (e.g. the SPE column) via a fluid connection, and should provide an environment which is suitable for the reaction. This will be known to those who are skilled in the art. The detection module may use a variety of different analytical techniques, for example, but not limited to optical, fluorescent, adsorption, colourimetric electrochemical or gravimetric approaches. In a preferred embodiment for the detection of propofol, the detection module comprises apparatus for absorption spectroscopy at wavelengths of 595 nm and 800 nm.

3. Addition of reagents to the reaction/detection module and inhibition of the reaction. Known volumes of some or all of the components of the reaction are then added to the reaction cell; these reagents may be introduced during the extraction step (i.e. as part of the SPE elution agent) or added after the extract is transferred to the reaction/detection cell. At this stage, the reaction is inhibited or the rate of reaction reduced using an appropriate method, for example, using one or more stimuli, including, but not limited to, temperature, pH, slow mixing, the absence or removal or one or more reactants and/or the addition of an inhibitor. Other methods of inhibition and/or reaction rate reduction will be known to those who are skilled in the art.

In a preferred embodiment, after elution of the propofol extract from whole blood using acetonitrile, the Gibbs reagent is added and the pH maintained below 8. In another embodiment, a weak low pH-buffer of suitable pH (e.g. pH≤8) can be included in the Gibbs reagent, added as a separate solution (before the Gibbs reagent) or incorporated in the acetonitrile solution used for elution from the SPE column. The low pH ensures propofol reacts very slowly with the Gibbs reagent. Examples of weak buffers include, but are not limited to, low concentrations of citric acid and formic acid. If required, after addition of all the required solutions, the reaction cell can then be mixed using methods including, but not limited to, agitation of the reaction cell, magnetic stirring and/or bubbling of a gas through the solution.

4. Acquisition of a reference measurement. In one embodiment of the invention, the reaction is inhibited/slowed down and the intended measurement technique applied to measure the solution in the absence of the desired reaction product. For example, in a preferred embodiment, absorption spectroscopy is used to measure the absorbance at 595 nm (A595) and 800 nm (A800) of a solution containing a whole blood propofol extract in acetonitrile and the Gibbs reagent at a pH of less than 8. Either a two wavelength measurement (for example, 595 nm and 800 nm), or an entire spectrum (for example, but not limited to, 400 nm to 800 nm) can be measured to collect these data. At a low pH, the kinetics of the Gibbs reaction at this pH are sufficiently slow, so the reaction can be considered inhibited. Here, the reference signal is established as the absorbance at 595 nm (indophenol peak absorbance) minus the absorbance at 800 nm (the 800 nm measurement is used to provide a correction for background optical scatter and incident light intensity variation in the sample). Other wavelengths than 800 nm (that are known to have zero or sufficiently low indophenol absorbance) may also be used to quantify the level of background scatter, these will be known to those who are skilled in the art. In another embodiment, for situations where the light intensity does not vary between the sample and reference measurement, it is not necessary to subtract the A800 signal, as the scatter contribution (due to particles in the cuvette) is measured at 595 nm during this low pH reference. In this case, only the absorbance at 595 nm needs to be recorded. It is noted that the term AX, where X is a positive number, is intended to denote the absorbance measured at a wavelength of X nm.

In another embodiment of the present invention, a number of measurements are made at various time points after mixing to monitor the evolution of the signal as the product is slowly produced. From these measurements the background response due to the initial "non-product" signal in the absence of the desired product can be determined, e.g. by curve fitting or extrapolation to the time when the reagents were added to the reaction mix.

5. Acquisition of the sample signal. After the background response(s) have been measured, the inhibiting mechanism is then removed to allow the desired reaction to move to equilibrium (or completion). Then, the same detection method as used in step 4 is employed to measure the signal from the desired reaction product plus the background response. Alternatively, if the reaction is too slow for equilibrium to be reached in a reasonable time, measurements at different times can be used to predict the concentration of the final product at equilibrium, e.g. by curve fitting or extrapolation to a time when equilibrium is felt to be reached.

For example, in a preferred embodiment aimed at detecting the propofol concentration in whole blood by the Gibbs/indophenol method, a known volume of a basic solution (e.g. buffer of suitably high pH, for example pH≥9.5) is added to the acetonitrile extract and the sample mixed thoroughly to increase the pH, preferably to a pH value greater than or equal to 9.5. If a buffer was added in the previous step to lower the pH and inhibit the reaction, the buffer used in this step must be sufficiently strong to overcome the low pH buffering action of the solution composition of Step 4. In a preferred embodiment, a 20 mM bicarbonate buffer at pH 9.6 is used to raise the pH and increase the rate of formation of the indophenol product. Other suitable buffering systems, or alternative methods of increasing the pH, will be known to those who are skilled in the art. This allows the Gibbs reaction to go to equilibrium (completion) and to produce a concentration of the indophenol product that is directly related to the original propofol concentration in whole blood. If the concentration of propofol in the blood sample is to be determined it is essential that the Gibbs reagent is in sufficient excess (relative to the concentration of propofol in the extract) to ensure that the concentration of the indophenol product in the reaction equilibrium is representative of the propofol concentration. As before, the difference in optical absorbance at 595 nm and 800 nm is determined. Either a two wavelength measurement (595 nm and 800 nm), or an entire spectrum (400 nm to 800 nm) can be measured to collect these data. In another embodiment, for situations where the light intensity does not vary between the sample and reference measurement, it is not necessary to measure the A800 signal, as the scatter contribution (due to particles in the cuvette) was measured at 595 nm during the low pH reference measurement.

6. Subtraction of the signal generated by the interfering species. In this step, the background ("non-product of interest") response obtained in step 4 can be used to remove the contribution of the interfering species to the signal obtained in step 5.

For example, in a preferred embodiment aimed at detecting the propofol concentration in whole blood by the Gibbs/indophenol method, the (A595-A800) absorbance signal at pH 7 is subtracted from the (A595-A800) absorbance signal at pH 9.6. This is known as the corrected indophenol absorbance signal. Alternatively, in another embodiment, for situations in which the full absorbance spectra are acquired (rather than a two-wavelength absorption measurement at 595 nm and 800 nm) during steps 4-5, the reference spectrum of step 4 is subtracted from the sample spectrum of step 5. The corrected indophenol absorbance signal is then calculated from this subtracted plot, by measuring the difference in absorbance at 595 nm and 800 nm.

In another embodiment, for situations where the incident light intensity does not vary between the sample and reference measurement, it is not necessary to use the A800 subtracted signals for the calculation of the corrected indophenol absorbance signal. This is because the scatter offset (due to particles in the cuvette) at 595 nm is measured during the low pH reference measurement. In all three embodiments described here, the final corrected indophenol absorbance signal is representative of the absorbance of the indophenol only, as the non-indophenol absorbance signals (e.g. protein, lipids and optical scatter) are present in both the reference and sample spectra. As there is a molar excess of Gibbs reagent in the sample, this corrected indophenol absorbance signal will be directly proportional to the propofol drug concentration in the blood sample being analysed. Comparison with a calibration curve constructed using known concentrations of the drug yield a precise and accurate estimate of the original drug concentration in the sample.

The measurement technique according to embodiments of the method of the present invention has significant advantages over the prior art; these advantages are most readily demonstrated in the case of the propofol measurements used as a preferred embodiment of the invention. First, the state-of-the-art in detecting low concentrations (<50 ng/ml) of propofol in whole blood is HPLC. The established Gibbs/indophenol method offers substantial savings over HPLC in equipment complexity, financial cost, sample preparation and time of measurement, but it has a relatively poor limit of detection (1 μg/ml). The present invention details reagents and methods for incorporating a background measurement in the absence of the indophenol product. This, in turn, confers a significant increase in sensitivity, and a decrease in the lower limit of detection, to the Gibbs/Indophenol technique as applied to extracts of whole blood, as it allows the removal of the variable offset in the background absorption/scattering signal. It also results in a significant simplification of the absorbance measurement instrumentation, as it only requires the use of a single wavelength (rather than an entire spectrum measurement as described in the prior art) for detection and concentration measurement. Therefore, this invention combines the benefits of the high sensitivity of detection afforded by HPLC with the simplicity of a measurement apparatus using the Gibbs/Indophenol technique. It allows consistent measurement of the propofol concentrations in whole blood down to <100 ng/ml. This, in turn, enables a simple, rapid and low cost assay that is uniquely suited to settings in which low concentrations of propofol are routinely measured (e.g. Intensive Care Units).

The method of the present invention may be utilized in an assay for the detection and concentration measurement of para-unsubstituted phenols, such as the anaesthetic propofol, in whole blood, where it provides a novel improvement of the solid phase extraction/Gibbs reaction assay described above. In a preferred embodiment, after transferring the post-solid phase extract into a reaction cell, the pH of the reaction is first controlled in order to effectively inhibit the reaction between the phenol and the Gibbs reagent.

This inhibition is achieved as the conversion of the Gibbs reagent (FIG. 2, A) to the activated form (FIG. 2, B) is effectively prevented at low pH (e.g. pH≤8). Although the reaction can proceed via alternative mechanisms, as for instance disclosed by I. Pallagi et al., "Mechanism of the Gibbs Reaction. Part 4.1: Indophenol Formation via N-Chlorobenzoquinone Imine Radical Anions. The Aza-SRN2 Chain Reaction Mechanism. Chain Initiation with 1,4-Benzoquinones and Cyanide Ion," *The Journal of Organic Chemistry*, vol. 64, 1999, pp. 6530-6540, the indophenol is produced at an extremely slow rate relative to the high pH situation, with time to equilibrium>1 h rather than on the order of <1 min for the high pH situation.

Therefore, over a period of a few minutes, the concentration of the indophenol in the sample is sufficiently small under these reaction conditions, for example close to zero or at least low enough not to affect the absorbance spectrum significantly, to perform additional absorbance measurement(s) in order to determine the background signal from any contaminating species in the absence of the coloured indophenol product. After the reference measurement(s) are performed, the pH of the extract is then increased (e.g. pH>9.5) and the reaction allowed to progress rapidly via the mechanism shown in FIG. 2. After the system reaches equilibrium, a sample spectrum is acquired, and the amount of indophenol product is quantified after subtraction of the appropriate reference data.

In another embodiment for the determination of propofol by the Gibbs/indophenol method, a single wavelength reference and sample measurement is performed (rather than an entire spectrum). In this case, only the absorbance signal at 595 nm is required to measure the contribution of any non-indophenol absorbance and optical scattering to the final signal. This makes the device considerably cheaper than the alternative entire spectrum (for example, 400 nm-800 nm) measurements described in the prior art such as by L. McGaughran et al.

It also enables real-time analysis of propofol concentrations in whole blood below 1 µg/ml in a PoC setting, thereby enhancing the utility of the assay in clinical settings, such as the ICU. Other applications for this embodiment include, but are not limited to, the analysis of low concentrations of phenolic compounds in biological fluids, waste water or food samples.

EXAMPLE

The present invention will be described in further detail by way of the following non-limiting example. In this example, the anaesthetic drug propofol is detected from whole blood using solid phase extraction (SPE) followed by a Gibbs reaction and detection by absorption spectroscopy. Established measurement protocols for low propofol concentrations rely on time consuming and complex HPLC-based assays. The low complexity and cost of the technique described in this example enables a propofol assay that can be performed in a near patient setting.

A blood sample (preferably 1 ml), which contains a known concentration propofol, is diluted 1:2 into water and then a known volume of this diluted sample, preferably 1.5 ml, is applied to a reverse-phase SPE column. The column is washed with (preferably (1.5 ml) of deionised water and (preferably 0.75 ml) of a 1:1 mixture of water and methanol to remove weakly bound impurities. The propofol extract is then eluted from the SPE column using a known volume (preferably 0.75 ml) of acetonitrile. The solid phase extraction of propofol into acetonitrile has been detailed by L. McGaughran et al. The eluent from the SPE column is then transferred to an optical absorption measurement cell, and a known volume (preferably 100 µl) and concentration (preferably 0.8 mmol·l$^{-1}$) of Gibbs reagent (FIG. 2, compound A) in methanol is added and mixed by bubbling of a known pressure of nitrogen gas (15 psi) through the cuvette. As the reaction between the Gibbs reagent and propofol is sufficiently slow, the concentration of indophenol product can be considered as being negligible at this point. The optical transmittance of the solution is then determined by measuring the spectrally dispersed intensity of the transmitted light (between 400 nm and 800 nm) through a known path length of the solution. This spectrum is the reference spectrum.

The transmitted intensities of the signals at 595 nm and 800 nm are recorded ($I_{ref,595nm}$ and $I_{ref,800nm}$, respectively).

Then, a known volume (preferably 100 µl) of 20 mM bicarbonate buffer at pH 9.6 is added to the cuvette and mixed using nitrogen gas bubbling as described above. The increase in the pH results in the conversion of the Gibbs reagent (FIG. 2, compound A) into the activated form (FIG. 2, compound B), which then reacts rapidly with the eluted propofol in the sample to produce the coloured indophenol product with an absorbance maximum at 595 nm. After a defined wait period (preferably 40s) to allow the reaction to reach equilibrium (and the concentration of the indophenol to reach a steady state), the transmitted intensity spectrum is measured, by recording the spectrally dispersed intensity of the transmitted light (between 400 nm and 800 nm) through the same known path length of the solution as before. Again, the transmitted intensities of the signals at 595 nm and 800 nm are recorded ($I_{s,595nm}$ and $I_{s,800nm}$ respectively). The absorbance of the indophenol product ($A_{final}$) is therefore defined by the Beer-Lambert Law (Equation 1).

$$[\text{Indophenol}] \propto A_{final} = \log\left(\frac{I_{ref,595\,nm}}{I_{s,595\,nm}}\right) - \log\left(\frac{I_{ref,800\,nm}}{I_{s,800\,nm}}\right) \quad \text{Equation 1}$$

This final absorbance is the absorbance of the indophenol product, corrected for the background absorbance at 595 nm from non-indophenol species (e.g. proteins, lipids carried over from the whole blood in the SPE extraction) and for background optical scatter due to turbidity in the sample (e.g. arising from insoluble aggregates). Therefore, this absorbance signal is directly proportional to the concentration of the final indophenol species and, assuming the reaction is in the steady state and an excess of Gibbs reagent, by inference the original concentration of propofol in the sample.

The results from this enhanced background subtraction scheme are shown in FIG. 3. Panel A shows a plot of absorbance versus wavelength obtained for a solid phase extract from a whole blood sample with an original propofol concentration of 0.8 m/ml. Inspection of the low pH reference spectrum (trace 2) relative to a methanol reference reveals that there is a significant non-indophenol absorbance at 595 nm. This produces an offset in the pH 9.6 sample spectrum (trace 1) relative to a methanol reference which is not attributed to indophenol. This offset will vary from sample to sample and should therefore be corrected for. Subtraction of the low pH reference spectrum from the pH 9.6 spectrum produces a final spectrum (trace 3) with an absorbance peak at 595 nm which is attributed to the absorbance of the indophenol only.

Panel B shows a final plot of absorbance versus predicted concentration data for the old methanol reference (trace 4) and the new low pH reference subtraction scheme (trace 5). The linear regressions and associated equations for the fit are also shown. Note the improvements in linearity and the reduction in the offset gained from the new low pH referencing scheme.

Using the normal subtraction method defined by McGaughran et al., Rapid measurement of blood propofol levels: A proof of concept study," *Journal of Clinical Monitoring and Computing*, vol. 20, 2006, pp. 381-381, in which the sample spectrum uses a "methanol only" sample in the cuvette as a reference (FIG. 3A, trace 1), there is a significant offset in absorbance due to the non-indophenol background in the spectrum. The additional reference measurement at low pH enables this "non-indophenol" background signal to be directly measured (FIG. 3A, trace 2) and then subtracted from the sample spectrum to obtain the spectrum of the indophenol only (FIG. 3A, trace 3).

Inspection of a plot of the final absorbance (Equation 1) versus the known propofol concentration reveals that this new subtraction scheme effectively reduces the measured absorbance and improves the linearity of the plot by removing the variable offset introduced by the varying background signal, as shown in FIG. 3B. It therefore allows the concentration of the indophenol product, and hence the original propofol concentration, to be more accurately determined for these very low concentration samples. Finally, note also the reduction in offset at 800 nm for the final subtracted spectrum (FIG. 3A, trace 3). This demonstrates that the low pH reference measurement accounts for the absorbance signal arising from to optical scatter. Therefore, a single wavelength measurement at 595 nm can be used to determine the propofol concentration rather than the entire spectrum (400 nm-800 nm) measurements described here. This will result in substantial savings in equipment complexity and cost.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A method of determining the presence of Propofol (2,6-di-isopropylphenol) by means of a detection of a reaction product between Propofol and an activated Gibbs reagent (2,6-dichloroquinoneimine), the method comprising:
   extracting the Propofol from a complex sample matrix;
   performing a background measurement on an initial reaction mixture comprising the Propofol extracted from the complex sample matrix and at most a negligible concentration of the reaction product, wherein the reaction conditions present in said initial reaction mixture at least reduce the reaction rate of the formation of the reaction product such that the background measurement can be performed without a measurable change in said negligible concentration;
   altering the reaction conditions in the initial reaction mixture to accelerate said reaction rate;
   continuing said reaction until the concentration of the reaction product has stabilized;
   performing a second measurement on the resultant reaction mixture to obtain a signal correlated to said concentration; and
   determining the presence of the Propofol from a difference between the background measurement and the second measurement.

2. The method of claim 1, wherein the step of determining the presence of Propofol comprises determining the concentration of Propofol in said reaction mixture.

3. The method of claim 1, further comprising controlling the reaction conditions present in the initial reaction mixture prior to performing said background measurement such that the background measurement can be performed without a measurable change in said at most negligible concentration.

4. The method of claim 3, wherein the step of controlling the reaction conditions present in the initial reaction mixture comprises controlling at least one of the pH, temperature, mixing rate and chemical composition of the initial reaction mixture.

5. The method of claim 4, wherein the step of controlling the chemical composition of the initial reaction mixture comprises withholding one of Propofol and the activated Gibbs reagent from the initial reaction mixture.

6. The method of claim 4, wherein the step of controlling the chemical composition of the initial reaction mixture comprises adding a reaction inhibitor to the initial reaction mixture.

7. The method of claim 1, wherein the first and second measurements are one of optical, fluorescent, adsorption, colorimetric, electrochemical and gravimetric measurements.

8. The method of claim 7, wherein:
   performing the background measurement comprises measuring at least a part of the absorption spectrum of the initial reaction mixture; and
   performing the second measurement comprises measuring at least a part of the absorption spectrum of the resultant reaction mixture.

9. The method of claim 1, wherein the initial reaction mixture comprises the Gibbs reagent (2,6 dichloroquinone-4-chloroimide), and wherein the reaction conditions in the initial reaction mixture comprise a pH that is sufficiently low to prevent the conversion of the Gibbs reagent into the activated Gibbs reagent, and wherein the step of altering the reaction conditions in the initial reaction mixture to accelerate said reaction rate comprises increasing the pH of the initial reaction mixture.

10. The method of claim 9, wherein the initial reaction mixture comprises a buffer solution to maintain the sufficiently low pH.

11. The method of claim 1, wherein the first and second measurements comprise determining the absorbance of the initial reaction mixture and the resultant reaction mixture respectively from an absorbance spectrum including the 400-800 nm interval.

12. The method of claim 1, wherein the first and second measurements comprise determining the absorbance of the initial reaction mixture and the resultant reaction mixture respectively at a first wavelength of 595 nm and a second wavelength of 800 nm.

13. The method of claim 1, wherein the first and second measurements comprise determining the absorbance of the initial reaction mixture and the resultant reaction mixture respectively at a wavelength of 595 nm only.

14. The method of claim 1, further comprising extracting the Propofol from the complex sample matrix using solid phase extraction.

15. The method of claim 14, wherein the complex sample matrix is blood.

16. The method of claim 15, wherein said extraction step comprises passing said blood sample over a solid phase extraction column, washing said column and eluting the Propofol using a suitable solvent.

17. The method of claim 16, wherein the solvent is acetonitrile.

18. The method of claim 16, wherein the blood sample is diluted with water to a ratio of greater than 1:1 prior to passing it over said column, said ratio preferably lying in a range of 1:2-1:50 blood:water.

19. The method of claim 1, further comprising performing at least one intermediate measurement following the step of altering the reaction conditions in the initial reaction mixture to accelerate said reaction rate and before the concentration of the reaction product has stabilized, wherein the step of determining the presence of the Propofol from a difference between the background measurement and the second measurement comprises measuring determining said presence from a difference between the background measurement, the second measurement and the at least one intermediate measurement.

20. The method of claim 10, wherein the buffer solution is a citric acid buffer, a formic acid buffer or a bicarbonate buffer.

\* \* \* \* \*